United States Patent [19]

Kurauchi et al.

[11] Patent Number: 5,959,139
[45] Date of Patent: Sep. 28, 1999

[54] PROCESS FOR PRODUCING OPTICALLY ACTIVE 2-HYDROXY-4-ARYLBUTYRIC ACID OR ITS ESTER

[75] Inventors: Masahiko Kurauchi; Yoshimasa Hagiwara; Hiroyuki Matsueda; Takashi Nakano; Kunisuke Izawa, all of Kawasaki, Japan

[73] Assignee: Ajinomoto Co., Inc., Tokyo, Japan

[21] Appl. No.: 08/698,730

[22] Filed: Aug. 16, 1996

[30] Foreign Application Priority Data

Aug. 22, 1995 [JP] Japan .................................. 7-213431
Jun. 19, 1996 [JP] Japan .................................. 8-192648

[51] Int. Cl.$^6$ .................................................. C07C 69/34
[52] U.S. Cl. .......................... 560/193; 560/192; 560/85; 562/470
[58] Field of Search ................................ 560/193, 192, 560/85; 562/470

[56] References Cited

FOREIGN PATENT DOCUMENTS

| 0 280 285 | 8/1988 | European Pat. Off. . |
| 0 329 156 | 8/1989 | European Pat. Off. . |
| 195 03 926 | 8/1996 | Germany . |
| 2 210 364 | 6/1989 | United Kingdom . |

OTHER PUBLICATIONS

Patent Abstarcts of Japan, vol. 15, No. 472 (C–0889), Nov. 29, 1991, JP–A–03 200739, Sep. 2, 1991.
Patent Abstracts of Japan, vol. 18, No. 75 (C–1163), Feb. 8, 1994, JP–A–05 286890, Nov. 2, 1993.
Chemical Abstracts 1967:16727, Cohen et al, Casoline printout, 1967.

*Primary Examiner*—Samuel Barts
*Attorney, Agent, or Firm*—Oblon, Spivak, McClelland, Maier & Neustadt, P.C.

[57] ABSTRACT

Provided is an industrially useful process for producing an optically active 2-hydroxy-4-arylbutyric acid or its ester. An optically active acyloxysuccinic anhydride is reacted with an aromatic compound in the presence of a Lewis acid to produce an optically active 2-acyloxy-4-oxo-4-arylbutyric acid. The 2-acyloxy-4-oxo-4-arylbutyric acid is converted to an optically active 2-acyloxy-4-arylbutyric acid through catalytic reduction. The 2-acyloxy-4-arylbutyric acid is hydrolyzed in the presence of an acid or an alkali to produce an optically active 2-hydroxy-4-arylbutyric acid. The 2-hydroxy-4-arylbutyric acid is reacted with an alcohol in the presence of an acid to produce an optically active 2-hydroxy-4-arylbutyric acid ester.

9 Claims, No Drawings

PROCESS FOR PRODUCING OPTICALLY ACTIVE 2-HYDROXY-4-ARYLBUTYRIC ACID OR ITS ESTER

BACKGROUND OF THE INVENTION

1. Field of the Invention

The present invention relates to a process for producing an optically active 2-hydroxy-4-arylbutyric acid or its ester, an intermediate for synthesis of enalapryl or cilazapryl which is known as an excellent anti-hypertensive agent. The present invention further relates to a process for producing an optically active 2-hydroxy-4-phenylbutyric acid or its ester.

2. Description of the Prior Art

Known processes for producing an optically active 2-hydroxy-4-phenylbutyric acid include:

(i) a process in which racemic 2-hydroxy-4-phenylbutyric acid is used as a starting material and is subjected to an enzymatic reaction in the presence of an acylating agent to obtain the (R)-isomer (Agric. Biol. Chem., 55, 293, 1991), (ii) a process in which racemic 2-hydroxy-4-phenylbutyric acid is formed into a salt with an optically active amine, and this salt is resolved using a difference in solubility in a diastereomer (EP 329,156), (iii) a process in which 2-oxo-4-phenylbutyric acid is asymmetrically reduced through an enzymatic reaction [J. Biotechnol., 24, 315 (1992)], (iv) a process in which 2-oxo-4-phenylbutyric acid is asymmetrically hydrogenated [Std. Surf. Sci. Catal., 78, 139 (1993)], (v) a process in which D-homophenylalanine is reacted with nitrous acid to form (R)-2-hydroxy-4-phenylbutyric acid (U.S. Pat. No. 5,225,408), (vi) a process in which benzalpyruvic acid is formed into (R)-2-hydroxy-4-phenyl-3-butenic acid using an L-proline-sodium boron hydride composite, and this butenic acid is then catalytically hydrogenated to form (R)-2-hydroxy-4-phenylbutyric acid [Japanese Laid-Open Patent Application (Kokai) No. 18,050/1992], (vii) a process in which a racemic 2-hydroxy-4-phenylbutyric acid ester is subjected to an enzymatic reaction to hydrolyze the (S)-isomer alone and obtain an ester of the (R)-isomer [Japanese Laid-Open Patent Application (Kokai) No. 225,499/1989], (viii) a process in which a racemic 2-acyloxy-4-phenylbutyric acid ester is subjected to an enzymatic reaction to deacylate the (R)-isomer alone and obtain the (R)-hydroxy compound [Japanese Laid-Open Patent Application (Kokai) No. 247,100/1989], (ix) a process in which a 2-oxo-4-phenylbutyric acid ester is asymmetrically reduced through an enzymatic reaction [Japanese Laid-Open Patent Application (Kokai) No. 328,984/1993], (x) a process in which racemic 2-hydroxy-4-phenylbutyric acid is optically resolved and then esterified [J. Chem. Soc., Perkin Trans. 1, 1011 (1986)], (xi) a process in which a 1-menthol ester of 2-oxo-4-phenylbutyric acid is synthesized, and then reduced [Tetrahedron Lett., 423 (1988)], and (xii) a process in which a 2-oxo-4-phenylbutyric acid ester is asymmetrically hydrogenated (EP 206,993 and EP 564,406).

However, the processes (i), (ii), (vii), (viii) and (x) using the racemic 2-hydroxy-4-phenylbutyric acid ester as a starting material are problematic in that the yield does not exceed 50%. Further, in the processes (iii), (iv), (ix), (xi) and (xii) using 2-oxo-4-phenylbutyric acid or its ester as a starting material, a step of forming the 2-oxo-4-phenylbutyric acid ester is intricate, and the yield is not satisfactory. In the process (v) using D-homophenylalanine as a starting material, the amino acid is itself not a natural-type amino acid, and therefore its production cost is high. Thus, this process is not practical.

Still further, since the process (vi) using benzalpyruvic acid as a starting material comprises two steps, it is intricate and entails a high cost.

SUMMARY OF THE INVENTION

It is an object of the present invention to provide an industrially practical process for producing an optically active 2-hydroxy-4-arylbutyric acid or its ester.

It has now been found that when an optically active acyloxysuccinic anhydride, which can easily be formed from optically active malic acid, is used as a starting material and is reacted with an aromatic compound in the presence of a Lewis acid as a catalyst, an optically active 2-acyloxy-4-oxo-4-arylbutyric acid which is a useful intermediate of an optically active 2-hydroxy-4-arylbutyric acid or its ester can easily be obtained. When this compound is further subjected to reduction, deacylation and esterification in this order, the above-mentioned problems can be solved.

Therefore, the present invention first relates to a process for producing an optically active 2-acyloxy-4-oxo-4-arylbutyric acid of formula (II):

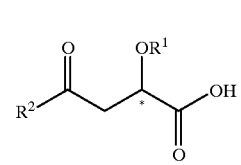

(II)

wherein:
$R^1$ represents a linear, branched or cyclic aliphatic acyl group having from 2 to 7 carbon atoms, which group is unsubstituted or substituted with a halogen atom, or is an aromatic acyl group having from 7 to 11 carbon atoms,
$R^2$ represents a substituted or unsubstituted aryl group, including a heteroaryl group, having from 4 to 12 carbon atoms, and
* represents an asymmetric carbon atom,
which comprises reacting optically active acyloxysuccinic anhydride of formula (I):

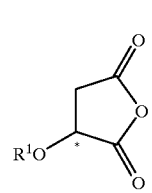

(I)

wherein $R^1$ and * are as defined above, with a substituted or unsubstituted aromatic compound having from 4 to 10 carbon atoms in the presence of a Lewis acid as a catalyst.

The aryl group may be a heteroaryl group which includes, but is not limited to those containing oxygen, nitrogen, and sulfur, for example furan.

The present invention further relates to a process for producing an optically active 2-hydroxy-4-arylbutyric acid of formula (III):

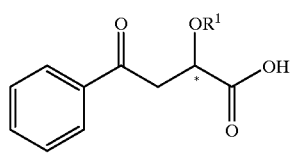

(V)

wherein R² and * are as defined in formula (II), which comprises subjecting an optically active 2-acyloxy-4-oxo-4-arylbutyric acid of formula (II) to catalytic reduction of the carbonyl group in the 4-position and elimination of the acyl group.

The present invention further relates to a process for producing an optically active 2-hydroxy-4-arylbutyric acid ester of formula (IV):

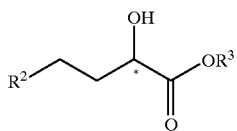

(IV)

wherein:
R² and * are as defined in formula (II), and
R³ represents a substituted or unsubstituted linear, branched or cyclic alkyl group having from 1 to 6 carbon atoms, or an aralkyl group having from 7 to 12 carbon atoms, which comprises subjecting an optically active 2-acyloxy-4-oxo-4-arylbutyric acid of formula (II) to catalytic reduction of the carbonyl group in the 4-position, elimination of the acyl group, and esterification with a substituted or unsubstituted linear, branched or cyclic alkyl alcohol having from 1 to 6 carbon atoms or with an aralkyl alcohol having from 7 to 12 carbon atoms.

The present invention further relates to optically active 2-acyloxy-4-oxo-4-phenylbutyric acid represented by formula (V)

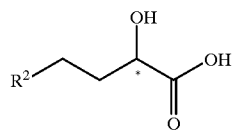

(III)

wherein R¹ and * are as defined in formula (II).

DETAILED DESCRIPTION OF THE PREFERRED EMBODIMENTS

The first process of the present invention is described below.

In this process, optically active acyloxysuccinic anhydride of formula (I) is reacted with an optically substituted aromatic compound having from 4 to 10 carbon atoms in the presence of a Lewis acid as a catalyst to produce an optically active 2-acyloxy-4-oxo-4-arylbutyric acid of formula (II).

The acyl group (R¹) in the optically active acyloxysuccinic anhydride of formula (I) may be a linear, branched or cyclic aliphatic acyl group having from 2 to 7 carbon atoms, which group is unsubstituted or substituted with a halogen atom or the like, or an aromatic acyl group having from 7 to 11 carbon atoms, such as an acetyl group, a trifluoroacetyl group or a benzoyl group. The acetyl group is industrially preferable in view of post-treatment and cost.

The optically active acyloxysuccinic acid of formula (I) can easily be formed through the reaction of optically active malic acid and halogenated acyl and/or an acid anhydride. For example, optically active acetoxysuccinic anhydride can easily be formed by reacting optically active malic acid with acetic anhydride in the presence of acetyl chloride [J. Org. Chem., 53, 1040 (1988)].

The aromatic compound which is the other starting material for producing the desired optically active 2-acyloxy-4-oxo-4-arylbutyric acid of formula (II) is an aromatic compound in the broad sense of the term. Examples of the aromatic compound include benzene, naphthalene, furan, thiophene, pyrrole, indole, and derivatives thereof. For example, in order to form an intermediate of enalapril which is one of the desired compounds in the present invention, benzene can be used.

Examples of the Lewis acid catalyst include anhydrous aluminum chloride, boron trichloride, and titanium tetrachloride. Anhydrous aluminum chloride is most preferable in view of the yield.

The conditions for the production of the desired optically active 2-acyloxy-4-oxo-4-arylbutyric acid of formula (II) are not particularly limited so long as the desired compound is produced.

For example, a reaction vessel is charged with optically active acyloxysuccinic anhydride of formula (I) and the aromatic compound in an amount which is equimolar to or larger than that of the compound of formula (I), preferably in an amount of from 1 to 10 mol per mol of the compound of formula (I). The solvent is added thereto to form a uniform solution. Then, the Lewis acid is added thereto in an amount of from 1 to 10 mils, preferably from 2 to 5 mils per mol of optically active acyloxysuccinic anhydride, and the mixture is stirred to produce the desired compound. When the amount of the aromatic compound based on optically active acyloxysuccinic anhydride is too small, the yield is reduced. When it is too large, the yield is reduced by the formation of side products, e.g., acetophenone. Further, when the amount of the Lewis acid based on optically active acyloxysuccinic anhydride is too small, the yield is reduced. When it is too large, this is wasteful.

The reaction can be conducted by first charging the Lewis acid and the solvent into a reaction vessel to form a solution or a suspension of the Lewis acid, and then adding optically active acyloxysuccinic anhydride and the aromatic compound. In this case, the amounts of the starting materials and the catalyst are exactly the same as the amounts mentioned above.

Any solvent can be used in this reaction (a kind of Friedel-Crafts reaction) so long as it does not adversely affect the reaction, and the starting materials can be dissolved to an extent required for the reaction. Examples of the solvent include methylene chloride, dichloroethane, benzene, nitrobenzene, and mixtures thereof. The amount of the solvent is not particularly limited so long as the reaction mixture can be effectively stirred. For example, it is usually from 1 to 100 parts by weight, preferably from 5 to 50 parts by weight per part by weight of optically active acyloxysuccinic anhydride as a starting material.

The reaction temperature is not particularly limited so long as the reaction proceeds and the product is not decomposed. However, at higher temperatures, side reaction occurs which decreases the reaction yield. Reaction temperature is therefore preferably from −70° C. to 30° C., more preferably from −40° C. to 0° C. When the temperature is too low, the reaction rate is decreased.

An aqueous solution of a mineral acid such as sulfuric acid, hydrochloric acid or the like is added to the reaction solution to stop the reaction, and the post-treatment is then conducted by a usual method in which layer separation, washing, extraction, concentration and crystallization are conducted as required, whereby the desired optically active 2-acyloxy-4-oxo-4-arylbutyric acid of formula (II) can easily be isolated. Usually, in the Friedel-Crafts reaction a gum substance derived from aluminum is precipitated in the post-treatment step, making it hard to conduct the reaction. However, in the process of the present invention, almost no gum substance is precipitated, and the reaction proceeds without this problem.

In the process of the present invention, the steric configuration of the optically active acyloxysuccinic anhydride used as the starting material becomes that of the resulting optically active 2-acyloxy-4-oxo-4-arylbutyric acid of formula (II) as it is. As a starting material of an anti-hypertensive agent such as the above-mentioned enalapril or cilazapril, a 2-acyloxy-4-oxo-4-arylbutyric acid of (R)-form which is obtained from starting (R)-malic acid is useful. However, when less costly (S)-malic acid is selected as starting material, this (S)-malic acid is esterified or hydrolyzed in the same manner as (R)-malic acid (see Example 6) to form a 2-hydroxy compound, and this compound is converted into a compound having a leaving group such as a methanesulfonyloxy group or the like. Further, the compound is reacted with an acyloxy anion to be able to invert the steric configuration; this compound can be used as a starting material of the above-mentioned anti-hypertensive agent.

The second process of the present invention is described below.

In this process, the optically active 2-acyloxy-4-oxo-4-arylbutyric acid of formula (II), which can be produced by the above-mentioned first process of the present invention, is subjected to catalytic reduction of the carbonyl group in the 4-position and elimination of the acyl group.

With respect to the reduction, for example, the optically active 2-acyloxy-4-oxo-4-arylbutyric acid of formula (II) is charged into the reaction vessel, and the solvent is added thereto to dissolve the compound of formula (II) therein. Catalyst is added to the solution, and catalytic reduction is conducted in a hydrogen atmosphere.

The solvent used in this reaction is not particularly limited, so long as it does not adversely affect the reaction and the starting material can be dissolved therein to an extent required for the reaction. Examples of the solvent include water, lower alcohols such as ethanol, lower aliphatic acids such as acetic acid, lower esters such as ethyl acetate, ether-type solvents such as tetrahydrofuran, and mixtures thereof. A reaction accelerator such as hydrochloric acid, sulfuric acid or the like may be added thereto as required. The amount of solvent is not particularly limited so long as the reaction mixture can effectively be stirred. For example, it is usually between 1 and 100 parts by weight, preferably between 5 and 50 parts by weight per part by weight of the optically active 2-acyloxy-4-oxo-4-arylbutyric acid of formula (II).

The catalyst to be used in the reduction is not particularly limited so long as the reaction can smoothly proceed. Examples of the catalyst include palladium, rhodium, ruthenium, platinum and nickel. These catalysts may be supported on carbon or the like, or contain water. The amount of the catalyst is not particularly limited, so long as the desired reaction can be completed. For example, it is usually between 0.01 and 10 mol, preferably between 0.1 and 5 mol per 100 mol of optically active 2-acyloxy-4-oxo-4-arylbutyric acid of formula (II).

The hydrogen pressure in the reduction is not particularly limited so long as the reaction can smoothly proceed. For example, it is usually between 1 and 150 kgf/cm$^2$, preferably between 1 and 20 kgf/cm$^2$.

The reaction temperature is not particularly limited so long as the reaction proceeds and the product is not decomposed. For example, it is usually between −20° C. and 120° C., preferably between 0° C. and 100° C.

After the completion of the reduction, the catalyst is removed by filtration, and the solvent is removed by distillation to obtain the optically active 2-acyloxy-4-arylbutyric acid in which the carbonyl group in the 4-position has been reduced.

Subsequently, the acyl group of this optically active 2-acyloxy-4-arylbutyric acid can be eliminated by, for example, hydrolyzing an acyloxy moiety with an appropriate hydrolyzing agent such as an acid or an alkali to remove the acyl group. In this manner, the desired optically active 2-hydroxy-4-arylbutyric acid of formula (III) can be obtained.

The hydrolysis can be conducted, for example, by adding water after completion of the above-mentioned reduction, and, if required, a water-miscible organic solvent such as a lower alcohol, acetone, or dioxane to a residue obtained by removing the catalyst and the solvent, and then further adding an acid or an alkali thereto.

The acid or the alkali used in the hydrolysis is not particularly limited, so long as the reaction can smoothly proceed. Examples thereof include sulfuric acid, hydrochloric acid, sodium hydroxide and potassium hydroxide.

After completion of the reaction, the post-treatment is conducted by a usual method in which concentration, extraction and washing are conducted in combination as required, and the product is purified through crystallization, distillation, or the like, whereby the desired optically active 2-hydroxy-4-arylbutyric acid of formula (III) can easily be isolated.

The third process of the present invention is described below.

In this process, the optically active 2-acyloxy-4-oxo-arylbutyric acid of formula (II) which can be formed by the above-mentioned first process of the present invention is subjected to catalytic reduction of the carbonyl group in the 4-position, elimination of the acyl group, and esterification with a substituted or unsubstituted linear, branched or cyclic alkyl alcohol having from 1 to 6 carbon atoms or with an aralkyl alcohol having from 7 to 12 carbon atoms, to produce the optically active 2-hydroxy-4-arylbutyric acid ester of formula (IV).

The reduction is conducted in exactly the same manner as in the above-mentioned second process of the present invention. The esterification is conducted by dissolving optically active 2-acyloxy-4-arylbutyric acid obtained from optically active 2-acyloxy-4-oxo-4-arylbutyric acid of formula (II) in a solvent ordinarily used in the esterification, for example, ethanol in case of an ethyl ester, adding an acid catalyst to the solution, and heat-refluxing the mixture. The acyl group is decomposed in the presence of the solvent under the above-mentioned conditions simultaneously with the esterification, and the desired optically active 2-hydroxy-4-arylbutyric acid ester of formula (IV) can be produced.

The amount of solvent is not particularly limited, so long as the reaction mixture can efficiently be stirred. For example, the amount of solvent is between 1 and 100 parts by weight, preferably between 5 and 50 parts by weight per part by weight of optically active 2-acyloxy-4-oxo-4-arylbutyric acid of formula (II).

The acid catalyst to be used in the esterification is not particularly limited, so long as the reaction can smoothly proceed. Examples of the acid catalyst include sulfuric acid, methanesulfonic acid, p-toluenesulfonic acid, and hydrogen chloride. The amount of the acid catalyst is not particularly limited, so long as the desired reaction can be completed. For example, it is usually between 0.1 and 100 mol, preferably between 1 and 30 mol per 100 mol of optically active 2-acyloxy-4-oxo-4-arylbutyric acid of formula (II).

After completion of the esterification, the post-treatment is conducted by a usual method in which concentration, extraction and drying are conducted in combination as required, and the product is purified through crystallization and distillation, whereby the desired optically active 2-hydroxy-4-arylbutyric acid ester of formula (IV) can easily be isolated like its free acid of formula (III).

When the reduction is conducted in the solvent which is used in the esterification, the reduction, the deacylation and the esterification can be conducted simultaneously to some extent.

Finally, the product which is described fourth in the present invention is mentioned below.

The optically active 2-acyloxy-4-oxo-4-arylbutyric acid of formula (II) of the present invention is a novel compound. The optically active 2-acyloxy-4-oxo-arylbutyric acid of formula (V), especially the compound in which the aryl group is a phenyl group and/or the asymmetric carbon provides the (R)-form, is useful as an intermediate for synthesis of enalapril or the like, as stated above.

Other features of the invention will become apparent in the course of the following descriptions of exemplary embodiments which are given for illustration of the invention and are not intended to be limiting thereof.

EXAMPLE 1

Production of (R)-2-acetoxy-4-oxo-4-phenylbutyric acid:

(R)-acetoxysuccinic anhydride (4.74 g) and 2.34 g of benzene were dissolved in 50 ml of methylene chloride, and the solution was cooled to −10° C. A suspension of 8 g of anhydrous aluminum chloride in 50 ml of methylene chloride was added to this solution in a dry argon atmosphere while being stirred carefully, lest the temperature of the solution should exceed 0° C. The mixture was stirred for 22 hours while maintaining the temperature of the solution at between −3° C. and 0° C., and 50 ml of 6-N hydrochloric acid were added thereto to stop the reaction.

The aqueous layer was separated, and the methylene chloride layer was washed with 50 ml of water. Then, methylene chloride was distilled off under reduced pressure. To the residue were added 50 ml of isopropyl acetate, and separated water was removed. Thereafter, isopropyl acetate was distilled off under reduced pressure to obtain 4.74 g of crude (R)-2-acetoxy-4-oxo-4-phenylbutyric acid as a light-yellow oily residue. When this crude product was allowed to stand at room temperature, it crystallized. The thus crystallized product was recrystallized from ether to give (R)-2-acetoxy-4-oxo-4-phenylbutyric acid as a white prism crystal.

$[\alpha]^{20}_D = -21.1°$ (c=1, ethanol); $^1$H NMR CDCl$_3$, δppm): 2.12 (s, 3H), 3.55 (dd, 1H, J=3.9Hz), 3.66 (dd, 1H, J=7.8), 5.75 (q, 1H), 7.48 (m, 2H), 7.62 (m, 1H), 7.96 (m, 2H); MS (ESI, m/z) 237.5 (MH+), 259.5 (M+Na+), 495.4 (2M+Na+). IR (KBr, cm$^{-1}$): 1760, 1702, 1688 (C═O); mp: 118–121° C.

EXAMPLE 2

Production of (S)-2-acetoxy-4-oxo-4-phenylbutyric acid:

(S)-acetoxysuccinic anhydride (15.81 g) and 23.43 g of benzene were dissolved in 150 ml of methylene chloride, and the solution was cooled to −20° C. Forty grams of anhydrous aluminum chloride were added to this solution in a dry argon atmosphere while being stirred carefully upon watching the increase in the temperature. The mixture was stirred for 6 hours while maintaining the temperature of the solution at −20° C. Thereafter, 100 ml of 1-N hydrochloric acid were added thereto carefully, lest the temperature should exceed 30° C., and the reaction was stopped.

The stirring was continued at room temperature until all the precipitated solids were dissolved. Then, the aqueous layer was separated, and methylene chloride was distilled off under reduced pressure. The residue was dissolved in 150 ml of isopropyl acetate, and washed with water. Subsequently, isopropyl acetate was distilled off under reduced pressure to obtain 19.86 g of crude (S)-2-acetoxy-4-oxo-4-phenylbutyric acid as a light yellow solid. This product was recrystallized from a mixed solution of ethanol and tert-butyl methyl ether to give (S)-2-acetoxy-4-oxo-4-phenylbutyric acid as a white prism crystal.

EXAMPLE 3

Production of (R)-2-acetoxy-4-oxo-4-phenylbutyric acid:

(R)-acetoxysuccinic anhydride (47.44 g) and 35.15 g of benzene were dissolved in 450 ml of methylene chloride, and the solution was cooled to −16° C. Anhydrous aluminum chloride (120.00 g) was added to this solution while being stirred carefully upon watching the increase in the temperature. The mixture was stirred for 6 hours while maintaining the temperature of the solution at −16° C. Thereafter, 300 ml of 1-N hydrochloric acid were added thereto carefully, lest the temperature should exceed 20° C., and the reaction was stopped.

The stirring was continued at room temperature until all the precipitated solids were dissolved. Further, 100 ml of isopropyl acetate were added thereto, and the mixture was stirred for a short period of time. Then, the aqueous layer was separated, and the organic layer was concentrated under reduced pressure. To the resulting slurry were added 450 ml of isopropyl acetate. The mixture was stirred until all the crystals were dissolved, then washed with water. The isopropyl acetate layer was concentrated under reduced pressure until the amount of the solution reached approximately 300 ml, and n-hexane was added thereto in the same volume as the concentrate. The mixture was cooled to 5° C., and stirred overnight at this temperature. The slurry was separated, and dried to obtain 62.70 g of (R)-2-acetoxy-4-oxo-4-phenylbutyric acid as a white crystal. HPLC analysis of the resulting product revealed that the purity (measured value based on a standard sample) was 100.8% and the optical purity was 100% ee.

EXAMPLE 4

Production of (S)-2-acetoxy-4-oxo-4-phenylbutyric acid:

Example 3 was repeated except that (R)-acetoxysuccinic anhydride was replaced with (S)-acetoxysuccinic anhydride to obtain 59.53 g of (S)-2-acetoxy-4-oxo-4-phenylbutyric acid as a white crystal. HPLC analysis of the resulting product revealed that the purity (measured value based on a standard sample) was 98.58% and the optical purity was 100% ee.

EXAMPLE 5

Production of ethyl (R)-2-hydroxy-4-phenylbutyrate:

Sixty grams of (R)-2-acetoxy-4-phenylbutyric acid were dissolved in 380 ml of ethanol, and 1.31 g of sulfuric acid and 5.41 g of 5% by weight palladium on carbon (water content 50%) were added thereto. The mixture was stirred in a hydrogen atmosphere at 20° C. for 20 hours. Palladium on carbon was separated through filtration, and 2.62 g of sulfuric acid were further added to the solution. The mixture was heat-refluxed for 16 hours. The solvent was distilled off under reduced pressure, and 380 ml of ethanol were added to the reside. The mixture was further heat-refluxed for 4 hours.

After completion of the reaction, ethanol was distilled off under reduced pressure. To the resulting oily residue were added 500 ml of isopropyl acetate. The mixture was washed with 250 ml of a 5% by weight aqueous sodium bicarbonate solution, then with 250 ml of water, and was concentrated under reduced pressure to obtain an isopropyl acetate solution of ethyl (R)-2-hydroxy-4-phenylbutyrate. HPLC analysis of the product revealed that the amount of ethyl (R)-2-hydroxy-4-phenylbutyrate was 48.02 g, the purity (area percentage) thereof was 99.8%, and the optical purity thereof was 100% ee.

EXAMPLE 6

Production of ethyl (S)-2-hydroxy-4-phenylbutyrate:

(S)-2-acetoxy-4-oxo-4-phenylbutyric acid (16.40 g) was dissolved in 100 ml of ethanol, and 0.35 g of sulfuric acid and 1.55 g of 5% by weight palladium on carbon (water content 50%) were added thereto. The mixture was stirred in a hydrogen atmosphere at 20° C. for 40 hours. Palladium on carbon was separated by filtration, and 0.71 g of sulfuric acid were further added to the solution. The mixture was heat-refluxed for 16 hours. The solvent was distilled off under reduced pressure, and 100 ml of ethanol were added to the residue. The mixture was further heat-refluxed for 4 hours.

After completion of the reaction, ethanol was distilled off under reduced pressure. To the resulting oily residue were added 140 ml of isopropyl acetate. The mixture was washed with 70 ml of a 5% by weight aqueous sodium bicarbonate solution and then with 70 ml of water, and was concentrated under reduced pressure to obtain an isopropyl acetate solution of ethyl (S)-2-hydroxy-4-phenylbutyrate. HPLC analysis of the product revealed that the amount of ethyl (S)-2-hydroxy-4-phenylbutyrate was 13.11 g, the purity (area percentage) thereof was 99.2%, and the optical purity thereof was 100% ee.

EXAMPLE 7

Production of (R)-2-hydroxy-4-phenylbutyric acid:

(R)-2-acetoxy-4-oxo-4-phenylbutyric acid (2.36 g) was dissolved in 15 ml of acetic acid, and 0.21 g of 5% by weight palladium on carbon (water content 50%) were added thereto. The mixture was stirred in a hydrogen atmosphere at 60° C. for 24 hours. Palladium on carbon was separated by filtration, and the solvent was then distilled off. Thirty milliliters of 1-N hydrochloric acid were added to the resulting (R)-2-acetoxy-4-phenylbutyric acid, and the mixture was heat-refluxed for 3 hours while being stirred.

The reaction solution was stirred in an ice bath while being cooled to precipitate (R)-2-hydroxy-4-phenylbutyric acid as a white crystal. This product was collected by filtration, and dried. The amount of dried (R)-2-hydroxy-4-phenylbutyric acid was 1.45 g, and the optical purity thereof was 100% ee.

EXAMPLE 8

Production of ethyl (R)-2-hydroxy-4-phenylbutyrate:

One gram of crude (R)-2-acetoxy-4-oxo-4-phenylbutyric acid obtained in Example 1 was dissolved in 10 ml of acetic acid, and 0.36 g of 5% by weight palladium on carbon (water content 50%) were added thereto. The mixture was stirred in a hydrogen atmosphere at 70° C. for 24 hours. Palladium on carbon was separated by filtration, and acetic acid was distilled off under reduced pressure. The residue containing (R)-2-acetoxy-4-phenylbutyric acid was dissolved in 25 ml of ethanol, and 4 droplets of sulfuric acid were added thereto as a catalyst. The mixture was heat-refluxed for 6 hours. Subsequently, ethanol was distilled off under reduced pressure, and 25 ml of ethanol were added thereto. The mixture was further heat-refluxed for 5 hours.

After completion of the reaction, ethanol was distilled off under reduced pressure. To the resulting oily residue were added 30 ml of isopropyl acetate. The mixture was washed with 25 ml of a 5% by weight aqueous sodium bicarbonate solution and then with 25 ml of water, and was dried over anhydrous magnesium sulfate. Magnesium sulfate was separated by filtration, and isopropyl acetate was then distilled off under reduced pressure to obtain 0.83 g of an oily residue containing ethyl (R)-2-hydroxy-4-phenylbutyrate. HPLC analysis of this residue revealed that the amount of ethyl (R)-2-hydroxy-4-phenylbutyrate was 64.5%.

EXAMPLE 9

Production of (R)-2-hydroxy-4-phenylbutyric acid:

One gram of crude (R)-2-acetoxy-4-oxo-4-phenylbutyric acid was reduced in the same manner as in Example 8 to obtain (R)-2-acetoxy-4-phenylbutyric acid. To this were added 15 ml of 1-N hydrochloric acid, and the mixture was heat-refluxed for 2 hours while being stirred.

When the reaction solution was analyzed by HPLC, it was found that 0.54 g of (R)-2-hydroxy-4-phenylbutyric acid were formed. The reaction solution was hot-filtered to remove small amounts of insoluble materials. Then, the residue was cooled in an ice bath to precipitate (R)-2-hydroxy-4-phenylbutyric acid as a white crystal. This product was collected through filtration, and dried. The amount of dried (R)-2-hydroxy-4-phenylbutyric acid was 0.45 g.

In accordance with the process of the present invention, a high-purity, optically active 2-hydroxy-4-arylbutyric acid or its ester can easily be produced in quite high yield. Therefore, the process of the present invention is an extremely advantageous process for producing optically active 2-hydroxy-4-arylbutyric acid or its ester, which is useful as an intermediate in the preparation of medications.

This application is based on Japanese Patent Application 213431/1995, filed with the Japanese Patent Office on Aug. 22, 1995, and Japanese Patent Application 192648/1996, filed with the Japanese Patent Office on Jun. 19, 1996, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing an optically active 2-acyloxy-4-oxo-4-arylbutyric acid of formula (II)

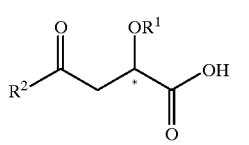

(II)

wherein:
   $R^1$ represents a linear, branched, or cyclic aliphatic acyl group having from 2 to 7 carbon atoms, wherein the acyl group is unsubstituted or substituted with a halogen atom, or is an aromatic acyl group having from 7 to 11 carbon atoms,
   $R^2$ represents a substituted or unsubstituted aryl group having from 4 to 12 carbon atoms, and
   * represents an asymmetric carbon atom,
which comprises reacting optically active acyloxysuccinic anhydride of formula (I):

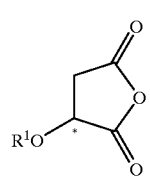

(I)

wherein $R^1$ and * are as defined above, with a substituted or unsubstituted aromatic compound having from 4 to 10 carbon atoms in the presence of a Lewis acid catalyst.

2. The process of claim 1, wherein $R^1$ is an acetyl group.

3. The process of claim 1, wherein $R^2$ is a phenyl group.

4. The process of claim 1, wherein the compounds of formulas (I) and (II) are (R)-isomers.

5. The process of claim 1, wherein the compound of formula (II) is (R)-2-acetoxy-4-oxo-4-phenylbutyric acid.

6. The process of claim 1, wherein the Lewis acid catalyst is anhydrous aluminum chloride.

7. The process of claim 1, wherein
said $R^1$ is an acetyl group;
said $R^2$ is a phenyl group;
said asymmetric carbon, *, has an (R) configuration;
said substituted or unsubstituted aromatic compound having from 4 to 10 carbon atoms is benzene; and
said Lewis acid catalyst is anhydrous aluminum chloride.

8. The process of claim 7, further comprising the steps of:
catalytically reducing the carbonyl group in the 4-position of said optically active 2-acyloxy-4-oxo-4-arylbutyric acid of formula (II); and
eliminating the acyl group to produce an optically active 2-hydroxy-4-arylbutyric acid of formula (III):

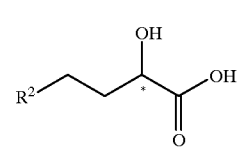

(III)

wherein $R^2$ is a phenyl group, and * represents an asymmetric carbon atom having and (R) configuration.

9. The process of claim 7, further comprising the steps of:
catalytically reducing the carbonyl group in the 4-position of said optically active 2-acyloxy-4-oxo-4-arylbutyric acid of formula (II);
eliminating the acyl group; and
esterifying with a substituted or unsubstituted linear, branched, or cyclic alkyl alcohol having from 1 to 6 carbon atoms, or with an arylalkyl alcohol having from 7–12 carbon atoms to produce an optically active 2-hydroxy-4-arylbutyric acid ester of the formula (IV):

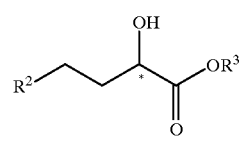

(IV)

wherein $R^2$ is a phenyl group,
$R^3$ is an ethyl group, and
* represents an asymmetric carbon atom having an (R) configuration.

* * * * *